(12) United States Patent
Sine et al.

(10) Patent No.: US 6,423,329 B1
(45) Date of Patent: *Jul. 23, 2002

(54) SKIN SANITIZING COMPOSITIONS

(75) Inventors: Mark Richard Sine, Morrow; Karl Shiqing Wei, Mason, both of OH (US); David Andrew Jakubovic, Staines (GB); Cheyne P. Thomas, Highland Heights; Michael Thomas Dodd, Florence, both of KY (US); Christopher Dean Putman, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/504,286

(22) Filed: Feb. 15, 2000

Related U.S. Application Data

(63) Continuation-in-part of application No. 09/321,291, filed on May 27, 1999, which is a continuation-in-part of application No. 09/249,717, filed on Feb. 12, 1999

(60) Provisional application No. 60/120,098, filed on Feb. 16, 1999.

(51) Int. Cl.[7] .......................... A61K 6/00; A61K 7/00; A61K 7/32; A01N 25/00

(52) U.S. Cl. ................. 424/405; 424/65; 424/401; 424/404; 424/405

(58) Field of Search .................. 424/65, 400, 405, 424/404, 443, 401

(56) References Cited

U.S. PATENT DOCUMENTS

| | | | |
|---|---|---|---|
| 2,054,989 A | 9/1936 | Moore | 167/58 |
| 3,485,915 A | 12/1969 | Gerstein et al. | 424/81 |
| 4,446,153 A | 5/1984 | Yang | 424/343 |
| 4,464,293 A | 8/1984 | Dobrin | 252/547 |
| 4,758,559 A | 7/1988 | Minetti | 514/844 |
| 4,800,076 A | 1/1989 | Bhat et al. | 424/69 |
| 4,906,458 A | 3/1990 | Shigeta et al. | 424/63 |
| 4,956,170 A | 9/1990 | Lee | 424/81 |
| 5,013,545 A | 5/1991 | Blackman et al. | 424/81 |
| 5,017,617 A | 5/1991 | Kihara et al. | 514/635 |
| 5,186,857 A | 2/1993 | Ramirez | 252/167 |
| 5,256,701 A | 10/1993 | Tamura et al. | 514/781 |
| 5,288,486 A | 2/1994 | White | 424/78.08 |
| 5,296,166 A | 3/1994 | Leong | 252/314 |
| 5,376,366 A | 12/1994 | Petchul et al. | 424/78.07 |
| 5,403,864 A | 4/1995 | Bruch et al. | 514/721 |
| 5,463,009 A | 10/1995 | Okada et al. | 528/15 |
| 5,484,597 A | 1/1996 | Slavtcheff et al. | 424/401 |
| 5,492,932 A | 2/1996 | Kundsin | 514/642 |
| 5,508,029 A | 4/1996 | Petchul et al. | 424/78.07 |
| 5,548,054 A | 8/1996 | Okada et al. | 528/25 |
| 5,591,442 A | 1/1997 | Diehl et al. | 424/401 |
| 5,599,533 A | 2/1997 | Stephniewski et al. | 424/78.02 |
| 5,618,522 A | 4/1997 | Kaleta et al. | 424/60 |
| 5,654,362 A | 8/1997 | Schultz et al. | 524/862 |
| 5,661,189 A | 8/1997 | Grieveson et al. | 514/784 |
| 5,700,898 A | 12/1997 | Okada et al. | 528/25 |
| 5,728,404 A | 3/1998 | von Rheinbaben et al. | 424/642 |
| 5,747,021 A | 5/1998 | McKenzie et al. | 424/73 |
| 5,750,579 A | 5/1998 | Kamishita et al. | 514/772.6 |
| 5,767,163 A | 6/1998 | Kundsin | 514/642 |
| 5,830,488 A | 11/1998 | Suzuki et al. | 424/405 |
| 5,833,973 A | 11/1998 | Dobkowski et al. | 424/18.08 |
| 5,849,314 A | 12/1998 | Dobkowski et al. | 424/401 |
| 5,854,336 A | 12/1998 | Divone, Sr. et al. | 524/588 |
| 5,871,718 A | 2/1999 | Lucas et al. | 424/65 |
| 5,919,437 A | 7/1999 | Lee et al. | 424/68 |
| 6,183,766 B1 * | 2/2001 | Sine et al. | 424/405 |

FOREIGN PATENT DOCUMENTS

| | | | |
|---|---|---|---|
| CA | 1224050 | 7/1987 | A61K/7/50 |
| CA | 1306953 | 9/1992 | A61K/7/48 |
| CA | 1319306 | 6/1993 | A61K/7/02 |
| CA | 2087140 | 7/1993 | A61K/7/50 |
| EP | 0 295 886 A2 | 12/1988 | A61K/7/02 |
| EP | 0 552 024 A2 | 7/1993 | A61K/7/06 |
| EP | 0 639 370 A1 | 2/1995 | A61K/7/40 |
| JP | Sho 63-20036 | 8/1989 | C08L/83/05 |
| JP | 04-005213 | 1/1992 | A61K/7/00 |
| JP | 05-58409 | 8/1993 | A61K/7/50 |
| KR | 97/042990 | 7/1997 | C11D/1/83 |
| WO | WO 95/05737 | 8/1993 | A61K/7/40 |
| WO | WO 96/02224 A1 | 2/1996 | A61K/7/00 |
| WO | WO 97/00667 | 1/1997 | A61K/7/48 |
| WO | WO 97/00668 | 1/1997 | A61K/7/48 |
| WO | WO 97/31619 | 9/1997 | A61K/7/48 |
| WO | WO 97/35475 | 10/1997 | A01N/31/02 |
| WO | WO 98/30096 A1 | 7/1998 | A01N/31/02 |

\* cited by examiner

Primary Examiner—Thurman K. Page
Assistant Examiner—S. Howard
(74) Attorney, Agent, or Firm—Marianne Dressman; Darryl C. Little; Tara M. Rosnell

(57) ABSTRACT

The present invention relates to compositions and methods of sanitizing and moisturizing skin surfaces.

25 Claims, No Drawings

SKIN SANITIZING COMPOSITIONS

CROSS-REFERENCE TO RELATED APPLICATION

This is a continuation-in-part of application U.S. Ser. No. 09/321,291, filed May 27, 1999, which is a continuation-in-part of U.S. Ser. No. 09/249,717, filed Feb. 12, 1999. In addition this application claims the benefit of U.S. Provisional Application No. 60/120,098 filed Feb. 16, 1999.

FIELD OF THE INVENTION

The present invention relates to compositions and methods of sanitizing and moisturizing skin surfaces.

BACKGROUND OF THE INVENTION

Today's consumers are well acquainted with the notion of germs and germ transmission. Daily, people come into contact with germs at eating establishments, the gym, while changing diapers or using portable toilet facilities (e.g., portapotties). Once in contact with human hands, these germs (i.e., micro-organisms such as bacteria, fungus and/or viruses) are quickly passed from individual to individual and, thus, contribute to the spread of contagious and/or infectious diseases. One of the best and easiest ways of preventing such germ and/or disease transmission is by routinely and conscientiously washing one's hands. Recognizing the inconvenience or impossibility of such hand washing under certain traveling conditions and/or time constraints, a number of manufacturers have introduced hand sanitizing products which sanitize skin surfaces without the need for water and/or towels.

Although current hand sanitizing products kill the germs associated with such routine activities as changing diapers or handling exercise equipment, they can fail to adequate moisturize the skin. Attempts at providing such moisturization have involved the use of humectant. However, effective amounts of humectant typically result in compositions having a sticky or tacky feel. The present inventors have found that skin sanitizing compositions comprising high concentrations of humectant and a detackifying agent provide excellent moisturization with improved skin feel.

The present inventors have also discovered that the detackifying agents of the present invention reduce the tack associated with thickening agents.

Therefore, an important aspect of the present invention is to provide skin sanitizing compositions providing moisturization and improved skin feel.

Another aspect of the present invention is to provide skin sanitizing compositions comprising high levels of humectant and a detackifying agent.

One other aspect of the present invention is to provide instant, hand sanitizing compositions comprising high levels of humectant and a detackifying agent selected from the group consisting of select silicones, wax materials having a melting point above about 20° C., powders, fluorochemicals and mixtures thereof.

These and other aspects will become readily apparent from the detailed description which follows.

SUMMARY OF THE INVENTION

The compositions of the present invention relates to skin sanitizing compositions, comprising:
 a.) an effective amount of sanitizing agent to kill or reduce the growth of microorganisms, the sanitizing agent comprising from about 40% to about 99% by weight of the composition of alcohol antiseptic;
 b.) from about 0.1% to about 15% of a humectant;
 c.) an effective amount of a detackifying agent selected from the group consisting of:
  i.) wax material soluble in the alcohol antiseptic and having a melting point greater than about 20° C.;
  ii.) silicones selected from the group consisting of nonvolatile silicones having a viscosity of at least about 15,000 centipoise, silicone elastomer, silicone elastomer/volatile silicone blends, silicone elastomer/nonvolatile silicone blends, nonvolatile/volatile silicone blends and mixtures thereof.
  iii.) powder;
  iv.) fluorochemicals; and
  v.) mixtures thereof;
 d.) optionally, from 0 to about 10% of thickener;
 e.) optionally, from 0 to about 20% of a lipophilic skin moisturizing agent;
 f.) optionally, from 0 to about 1% of perfume; and
 g.) from about 0 to about 60% water.

The skin sanitizing compositions of the present invention are suitable for use in leave-on or rinse-off products.

The present invention further relate to methods of using the skin sanitizing compositions.

DETAILED DESCRIPTION OF THE INVENTION

The skin sanitizing compositions of the present invention can comprise, consist of, or consist essentially of the essential elements and limitations of the invention described herein, as well any of the additional or optional ingredients, components, or limitations described herein.

All percentages, parts and ratios are based upon the total weight of the personal cleansing compositions of the present invention, unless otherwise specified. All such weights as they pertain to listed ingredients are based on the active level and, therefore, do not include carriers or by-products that may be included in commercially available materials, unless otherwise specified.

By the term "alcohol antiseptic" as used herein, means an alcohol (or combination of alcohols) which is effective, at the concentration employed, to kill microorganisms, for example, bacteria, with which it comes in contact.

By the term "instant" as used herein means the compositions of the present invention disinfect the skin area within 30 seconds, preferably 20 seconds without the need for soap and water.

Preferably the sanitizing and moisturizing compositions of the present invention are clear. The term "clear" as defined herein means transparent or translucent, preferably transparent as in "water clear," when observed through a layer having a thickness of less than about 10 cm.

The skin sanitizing compositions of the present invention, including the essential and optional components thereof, are described in detail hereinafter.

Essential Components

Alcohol Antiseptic

The compositions of the present invention also contain from about 40% to about 99%, more preferably from about 50% to about 80%, most preferably from about 55% to about 80% of a alcohol antiseptic or mixtures thereof. Examples of suitable alcohol antiseptics include, but are not limited to, ethanol, n-propanol and isopropanol and mixtures thereof. Preferred for use herein is ethanol.

Humectant

Another essential ingredient of the present invention is the humectant. Humectants serve to retain water on the skin surface. Examples of preferred humectants include polyhydric alcohols selected from the group consisting of ethylene glycol, propylene glycol, dipropylene glycol, butylene glycol, hexylene glycol, polyethylene glycols, glycerin sorbitol, panthenols, urea, alkoxylated glucose derivatives, such as Glucam (RTM) E-20, hexanetriol, glucose ethers, sodium hyaluronate, soluble chitosan and mixtures thereof. Glycerin is presently preferred.

The glycerin used in this invention is preferably "glycerin, USP, 99.5%", most preferably that which is sold by Dow Chemical, Inc., Emery Industries, Inc. (under the name "Superol 99.5%"), and Procter & Gamble. Another preferred humectant is "DL-panthenol", which is sold by Hoffman-Laroche. Yet another preferred humectant is PEG/PPG 17/6 copolymer (17 moles ethylene oxide/6 moles propylene oxide), preferably that sold by PPG/Mazer Chemicals or Union Carbide, under the names "Macol 450" and "Ucon 75-H-450". Still another preferred humectant is phytantriol, preferably that sold by Roche. Also preferred are polyglycerylmethacrylate lubricants having a viscosity at 25° C. of 300,000 to 1,100,000 mPa.s; a specific gravity at 25° C. of 1 to 1.2 g/ml, a pH of 5.0 to 5.5; a bound water content of 33 to 58%; and, a free water content from 5 to 20%. Suitable polyglycerylmethacrylate lubricants are marketed by Guardian Chemical Corporation under the trademark "Lubrajel". The "Lubrajels" identical as "Lubrajel DV", "Lubrajel MS", and "Lubrajel CG" are preferred in the present invention. Preferred Polyethylene glycols have weight average molecular weights less than about 6000.

Humectants are preferably present in the compositions of the present invention at concentrations of from about 0.1% to about 15%, preferably from about 1% to about 8%, more preferably from about 3% to about 6%.

Detackifying Agent

Also essential to the compositions of the present invention are detackifying agents at an effective amount to reduce the stickiness or tack associated with humectants and/or gelling agents. The term "detackifying agent," as used herein, means an agent which prevents, reduces and/or eliminates the sticky or tacky feeling typically associated with humectants. Detackifying agents suitable for use in the present invention are selected from the group consisting of wax material soluble in the alcoholic antiseptic and having a melting point greater than about 20° C.; select silicones; powders; fluorochemicals and mixtures thereof.

i.) Wax Materials

Wax materials used herein preferably have melting points of at least about or greater than about 20° C., more preferably at least about or greater than about 25° C., and still more preferably at least about or greater than about 32° C., and most preferably at least about or greater than about 35° C. The wax materials are preferably soluble in the alcohol antiseptic. The phrase "soluble in the alcohol antiseptic," as used herein, means the wax materials is soluble in the alcohol antiseptic, at 25° C., at a concentration of 0.1%, preferably 0.2%, more preferably 0.4% by weight, and most preferably soluble at 1.0% by weight. Examples of suitable wax materials include, but are not limited to, dimethicone copolyols having a weight average molecular weight greater than about 1000 such as Biowax®.(supplied by Biosil), polyoxyethylene glycols having weight average molecular weight greater than about 500 such as Carbowax (supplied by Union Carbide), and mixtures thereof. Preferred for use herein is Biowax® 754.

Also preferred for use herein are polyoxyethylene glycols having weight average molecular weight greater than about 500, preferably from about 1000 to about 10,000, more preferably from about 1400 to about 6000. Most preferred is PEG-32 (Carbowax 1450).

When present, the above wax materials preferably comprise from about 0.1% to about 10%, preferably from about 0.1% to about 5%, most preferably from about 0.4% to about 2% by weight of the composition.

ii.) Silicones

Useful as detackifying agents in the present invention are volatile and non-volatile silicone oils. The term "nonvolatile" as used herein means that the silicone has a boiling point of at least about 260° C., preferably at least about 275° C., more preferably at least about 300° C. Such materials exhibit very low or no significant vapor pressure at ambient conditions. The term "volatile" as used herein mean that the silicone has a boiling point of from about 99° C. to about 260° C.

Volatile silicones suitable for use in the present invention are disclosed in U.S. Pat. No. 4,781,917, issued to Luebbe et al., Nov. 1, 1988 and U.S. Pat. No. 5,759,529 to LeGrow et al., issued Jun. 2, 1998, both of which are herein incorporated by reference in their entirety. Additionally, a description of various volatile silicones materials is found in Todd et al., "Volatile Silicone Fluids for Cosmetics", Cosmetics and Toiletries, 91:27–32 (1976). Preferred silicones have surface tensions of less than about 35 dynes, more preferably less than about 30 dynes, most preferably less than about 25 dynes. Particularly preferred volatile silicone oils are selected from the group consisting of cyclic volatile silicones corresponding to the formula:

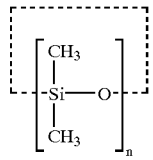

wherein n is from about 3 to about 7; and linear volatile silicones corresponding to the formula:

wherein m is from about 1 to about 7. Linear volatile silicones generally have a viscosity of less than about 5 centistokes at 25.degree. C., whereas the cyclic silicones have viscosities of less than about 10 centistokes at 25.degree. C. Highly preferred examples of volatile silicone oils include cyclomethicones of varying viscosities, e.g., Dow Corning 200, Dow Coming 244, Dow Coming 245, Dow Coming 344, and Dow Corning 345, (commercially available from Dow Coming Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.). When present in the compositions of the present invention, volatile silicones comprise at least about or greater than about 3% to about 10%, more preferably from about 4% to about 8%, and most preferably from about 6% to about 8% by weight of the present invention.

Also useful as the detackifying agent are nonvolatile silicones such as fluid silicones and gum silicones. The molecular weight and viscosity of the particular selected silicone will determine whether it is a gum or a fluid. The term "silicone fluid," as used herein, denotes a silicone with viscosities ranging from about 5 to about 600,000 centistokes, most preferably from about 350 to about 100,000 centistokes, at 25° C. The term "silicone gum," as used herein, denotes silicones with mass molecular weights of from about 200,000 to about 1,000,000 and with a viscosities greater than about 600,000 centistokes. Non-volatile silicones of the present invention preferably have a viscosity of at least about 15,000 centipoise.

Suitable non-volatile silicones include polysiloxanes and other modified silicones. Polysiloxanes and other modified silicones are described in U.S. Pat. Nos. 5,650,144 and 5,840,288, both of which are herein incorporated by reference in their entirety. Examples of suitable polysiloxanes and modified silicones include, but are not limited to, polyalkylsiloxanes, polyarylsiloxanes, polyalkylarylsiloxanes, polyestersiloxanes, polyethersiloxane copolymers, polyfluorosiloxanes, polyaminosiloxanes, and mixtures thereof. Preferred non-volatile polysiloxanes are polydimethylsiloxane having viscosities of from about 5 to about 100,000 centistokes at 25° C.

Silicone fluid and gum mixtures or blends can also be used. Silicone gum and fluid blends are disclosed in U.S. Pat. No. 4,906,459, Cobb et al., issued Mar. 6, 1990; U.S. Pat. No. 4,788,006, Bolich, Jr. et al., issued Nov. 29, 1988; U.S. Pat. No. 4,741,855, Grote et al., issued May 3, 1988; U.S. Pat. No. 4,728,457, Fieler et al., issued Mar. 1, 1988; U.S. Pat. No. 4,704,272, Oh et al., issued Nov. 3, 1987; and U.S. Pat. No. 2,826,551, Geen, issued Mar. 11, 1958; U.S. Pat. No. 5,154,849, Visscher et al., issued Oct. 13, 1992, all of which are herein incorporated by reference in their entirety.

When present in the compositions of the present invention, non-volatile silicones comprise from about 0.01% to about 5%, preferably from about 0.1% to about 2%, more preferably from about 0.1% to about 1% by weight of the present invention.

Silicone elastomers are also useful as detackifying agents in the present invention. Suitable silicone elastomers are illustrated in U.S. Pat. No. 5,654,362, herein incorporated by reference in its entirety. Examples of suitable elastomers include, but are not limited to, dimethicone crosspolymer, dimethicone/vinyldimethicone crosspolymer, polysilicone-11 and mixtures thereof. Such elastomers can be used alone or with volatile or nonvolatile solvents Examples of suitable solvents include, but are not limited to, volatile silicones, volatile alcohols, volatile esters, volatile hydrocarbons, and mixtures thereof. The silicone elastomers are crosslinked and preferably have a weight average molecular weight greater than about 100,000. Preferred for use herein are elastomer/solvent blends having an elastomer to solvent ratio of from about 1:100 to about 1:1, more preferably from about 1:30 to about 1:5. Preferably the silicone elastomer blend has a viscosity of from about 50,000 centipoise to about 400,000 centipoise, more preferably from about 100,000 centipoise to about 300,000 centipoise.

Examples of suitable silicone elastomer blends include cyclomethicone and dimethicone crosspolymer blend (Dow Corning®9040 silicone elastomer); cyclomethicone and dimethicone/vinyldimethicone cross polymer blend (SFE 839 elastomer dispersion available from GE); octamethylcyclotetrasiloxane and polysilicone-11 blend (Gransil GCM available from Shin Etsu) and mixtures thereof. Preferred herein is cyclomethicone and dimethicone/vinyldimethicone cross polymer blend.

When present, the silicone elastomer preferably comprises from about 0.01% to about 5%, preferably from about 0.1% to about 2%.

When present, silicone elastomer or gum blends preferably comprise from about 0.1% to about 10%, preferably from about 1% to about 10%, most preferably from about 4% to about 10% by weight of the composition.

iii.) Powders

Also useful as detackifying agents are powders. Powder ingredients which may be compounded in the composition of the present invention include inorganic powder such as gums, chalk, Fuller's earth, talc, kaolin, iron oxide, mica, sericite, muscovite, phlogopite, synthetic mica, lepidolite, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, fumed silica, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, polyethylene powder, methyl polymethacrylate powder, polystyrene powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as titanium dioxide, zinc oxide, and magnesium oxide. Other useful powders are disclosed in U.S. Pat. No. 5,688,831, to El-Nokaly et al., issued Nov. 18, 1997, herein incorporated by reference in its entirety. Preferred for use herein are particulate crosslinked hydrocarbyl-substituted polysiloxane available under the tradename Tospearl from Toshiba Silicone. Mixtures of the above powders may also be used.

Preferably the powders of the present invention have a particle size such that the average chord length of the powder particles range from about 0.01 microns to about 100 microns, preferably from about 0.1 microns to about 50 microns, more preferably from about 1 micron to about 20 microns.

The powders of the present invention preferably have a refractive index equal to the refractive index of the alcohol antiseptic. The powders of the present invention can be spherical or platelet in shape for smooth skin feel. Alternatively, the powders can be amorphous or irregular shaped for a draggy skin feel. When present, powders preferably comprise from about 0.01% to about 10%, preferably from about 0.1% to about 10%, more preferably from about 0.1% to about 5%, most preferably from about 0.4% to about 2% by weight of the composition.

iv.) Fluorochemicals

Also useful herein are fluorochemicals. These fluorochemicals include fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. More specific examples of such liquid carriers include, but are not limited to, perfluoropolymethyl isopropyl ethers, perfluoropolypropylethers, acrylamide fluorinated telomer or mixtures thereof. Other more specific examples include, but are not limited to, the polyperfluoroisopropyl ethers available from Dupont Performance Chemicals under the trade name Fluortress® PFPE oils.

When present, powders preferably comprise from about 0.01% to about 10%, preferably from about 0.1% to about 2% by weight of the composition.

Whilst some materials can function either as the lipophilic skin moisturizing agent, thickening agent therefor, or degreasing agent, it will be appreciated that the moisturizing, thickening and degreasing function cannot be provided by the same component. However, it will be understood that where the composition comprises three or more lipophilic skin moisturizing agents, two of said lipophilic skin moisturizing agents can also function as a thickening agent or degreasing agent.

Water

The personal cleansing compositions of the present invention comprise from about 0% to about 70%, preferably from about 10% to about 50%, more preferably from about 20% to about 50%, by weight of water.

Optional Components

Cyclodextrin

Optionally, but preferably, cyclodextrin can be added to the compositions of the present invention. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of 1% (1 gram in 100 grams of water).

Non-derivatised beta-cyclodextrin can be present at a level up to its solubility limit of about 1.85% at room temperature. When beta-cyclodextrin is applied to a wipe substrate, levels higher than its solubility limit can be used.

Highly water-soluble cyclodextrins are also preferred to be used in the present invention, such as, alpha-cyclodextrin and/or derivatives thereof, gamma-cyclodextrin and/or derivatives thereof, derivatised beta-cyclodextrins, and/or mixtures thereof. Highly water-soluble cyclodextrins are those having water solubility of at least about 10 g in 100 ml of water at room temperature, preferably at least about 20 g in 100 ml of water, more preferably at least about 25 g in 100 ml of water at room temperature. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl groups, such as hydroxypropyl cyclodextrins and/or hydroxyethyl cyclodextrins, wherein R is a —$CH_2$—$CH(OH)$—$CH_3$ or a —$CH_2CH_2$—$OH$ group; those with (hydroxyalkyl)alkylenyl bridging groups such as cyclodextrin glycerol ethers wherein (2-hydroxyethyl)ethylenyl, —$CH_2CH(CH_2OH)$—, groups bridge between the 2' and 3' hydroxyl oxygens on the glucosyl units; branched cyclodextrins such as maltose-bonded cyclodextrins; cationic cyclodextrins such as those containing 2-hydroxy-3-(dimethylamino)propyl ether, wherein R is $CH_2$—$CH(OH)$—$CH_2$—$N(CH_3)_2$ which is cationic at low pH; quaternary ammonium, e.g., 2-hydroxy-3-(trimethylammonio)propyl ether chloride groups, wherein R is $CH_2$—$CH(OH)$—$CH_2$—$N^+(CH_3)_3Cl^-$; anionic cyclodextrins such as carboxymethyl cyclodextrins, cyclodextrin sulfobutylethers, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydrocyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, herein incorporated by reference; and mixtures thereof. Other cyclodextrin derivatives are disclosed in U.S. Pat. No. 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; U.S. Pat. No. 5,534,165, Pilosof et al., issued Jul. 9, 1996, all of said patents being incorporated herein by reference.

Cyclodextrins particularly preferred for use herein are alpha-cyclodextrin, beta-cyclodextrin, hydroxypropyl alpha-cyclodextrin, hydroxypropyl beta-cyclodextrin, methylated alpha-cyclodextrin, methylated beta-cyclodextrin, and mixtures thereof. More preferred for use herein are alpha-cyclodextrin, beta-cyclodextrin, hydroxypropyl beta-cyclodextrin, hydroxypropyl alpha-cyclodextrin, methylated beta-cyclodextrin, methylated alpha-cyclodextrin and mixtures thereof.

Typical levels of cyclodextrin are from about 0.1% to about 10%, preferably from about 0.2% to about 4%, more preferably from about 0.3% to about 3%, most preferably from about 0.4% to about 2%, by weight of the composition.

Other useful odor control agents include, but are not limited to, water soluble metallic salt, zeolites, soluble carbonate and/or bicarbonate salts, water soluble ionic polymers, silica gel, silica molecular sieves, activated alumina, kieselguhr, fullers earth, montmorillonite, smectite, attapulgite, bentonite, palygorskite, kaolinite, illite, halloysite, hectorite, beidellite, nontronite, saponite, hormite, vermniculite, sepiolite, chlorophyll, soda lime, calcium oxide, chitin, potassium permanganate, and activated charcoal or activated carbon. Mixtures of any of the above odor control agents can also be used.

Metallic Salt

Optionally, but preferably, metallic salt, preferably water-soluble zinc salts, can be added to the composition of the present invention. A water-soluble metallic salt can be used as an odor control agent. A water-soluble metallic salt can be present in the freshening composition of the present invention to absorb amine and sulfur-containing compounds. Furthermore, they usually do not contribute an odor of their own. Preferably the water-soluble metallic salts are selected from the group consisting of copper salts, zinc salts, and mixtures thereof.

The preferred zinc salts have been used most often for their ability to ameliorate malodor, e.g., in mouth wash products, as disclosed in U.S. Pat. No. 4,325,939, issued Apr. 20, 1982 and U.S. Pat. No. 4,469,674, issued Sep. 4, 1983, to N. B. Shah, et al., incorporated herein by reference. U.S. Pat. No. 3,172,817, issued to Leupold, et al., discloses deodorizing compositions containing slightly water-soluble salts of an acyl-acetone with a polyvalent metal, including copper and zinc salts. Said patents are incorporated herein by reference.

Examples of preferred water-soluble zinc salts are zinc chloride, zinc gluconate, zinc lactate, zinc maleate, zinc salicylate, zinc sulfate, etc. Highly-ionized and soluble zinc salts such as zinc chloride, provide the best source of zinc ions. Examples of preferred copper salts are copper chloride and copper gluconate. Preferred metallic salts are zinc chloride and copper chloride.

Metallic salts are added to the composition of the present invention typically at a level of from about 0.1% to about 10%, preferably from about 0.2% to about 7%, more preferably from about 0.3% to about 5%, by weight of the composition. When zinc salts are used as the metallic salt, and a clear solution is desired, it is preferable that the pH of the solution is adjusted to less than about 7, more preferably less than about 6, most preferably, less than about 5, in order to keep the solution clear. Mixtures of the metallic salts and odor control agents can also be used.

Thickener

Optionally, but preferably, thickeners can be added to the composition of the present invention. Examples of suitable thickeners include, but are not limited to, naturally-occurring polymeric materials such as sodium alginate, xanthan gum, quince seed extract, tragacanth gum, starch and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Inorganic thickeners may also be used such as aluminium silicates, such as, for example, bentonites, or a mixture of polyethylene glycol and polyethylene glycol stearate or distearate.

Also useful herein are hydrophilic gelling agents such as the acrylic acid/ethyl acrylate copolymers and the carboxyvinyl polymers sold by the B.F. Goodrich Company under the trademark of Carbopol Registered TM resins. These resins consist essentially of a colloidally water-soluble polyalkenyl polyether crosslinked polymer of acrylic acid crosslinked with from 0.75% to 2.00% of a crosslinking agent such as polyallyl sucrose or polyally pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name Carbopol Ultrez 10, Carbopol ETD2020, Carbopol 1382, Carbopol 1342, Salcare SC96 (Polyquaternium-37 and Propylene Glycol Dicaprylate/Dicaprate and PPG-1 Trideceth-6), Stabileze QM (Polyvinylmethacrylate/Methacrylic acid Decadiene crosspolymer), Stabylen 30 (acrylate/vinyl isodecanoate crosspolymer) and Pemulen TR-1 (CTFA Designation: Acrylates/10-30 Alkyl Acrylate Crosspolymer). Combination of the above polymers are also useful herein. Other gelling agents suitable for use herein include oleogels such as trihydroxystearin and aluminum magnesium hydroxy stearate. Another useful thickener for the present invention is the non-ionic polymer under the CTFA designation: polyacrylamide and isoparrafin and laureth-7, available as Sepigel from Seppic Corporation.

Hydrophobically modified celluloses are also suitable for use herein. These celluloses are described in detail in U.S. Pat. Nos. 4,228,277 and 5,104,646, both of which are herein incorporated by reference in their entirety.

Preferred for use herein are carbomers such as Carbopol 980, Carbopol 940, Carbopol Ultrez 10, Carbopol ETD2020 and mixtures thereof.

The thickener is preferably present at a concentration of from about 0.01% to about 10%, preferably from about 0.1% to about 5%, more preferably from about 0.1% to about 1% and even more preferably from about 0.1% to about 0.5%. Mixtures of the above thickeners may also be used.

Lipophilic Skin Moisturizering Agents

Lipophilic skin moisturizing agents/emollients may also be incorporated into the present invention. Examples of suitable lipophilic skin moisturizers include, but are not limited to, petrolatum, mineral oil, micro-crystalline waxes, polyalkenes, paraffin, cerasin, ozokerite, polyethylene, perhydrosqualene, dimethicones, cyclomethicones, alkyl siloxanes, polymethylsiloxanes, methylphenylpolysiloxanes, hydroxylated milk glyceride, castor oil, soy bean oil, maleated soy bean oil, satffower oil, cotton seed oil, corn oil, walnut oil, peanut oil, olive oil, cod liver oil, almond oil, avocado oil, palm oil, sesame oil, liquid sucrose octaesters, blends of liquid sucrose octaesters and solid polyol polyesters, lanolin oil, lanolin wax, lanolin alcohol, lanolin fatty acid, isopropyl lanolate, acetylated lanolin, acetylated lanolin alcohols, lanolin alcohol linoleate, lanolin alcohol riconoleate, beeswax, beeswax derivatives, spermaceti, myristyl myristate, stearyl stearate, carnauba and candelilla waxes, cholesterol, cholesterol fatty acid esters and homologs thereof, lecithin and derivatives, Sphingo lipids, ceramides, glycosphingo lipids and homologs thereof, and mixtures thereof. A more detailed discussion of useful lipophilic skin moisturizers can be found in U.S. Pat. No. 5,716,920 to Glenn, Jr. et al., issued Feb. 10, 1998, herein incorporated by reference in its entirety.

Also useful as a lipophilic skin moisturizing agent are liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S. Pat. Nos. 5,306,514, 5,306,516 and 5,306,515 to Letton; all issued Apr. 26, 1994, all of which are herein incorporated by reference.

When incorporated in the compositions of the present invention, the lipophilic skin moisturizer is present at concentrations of from about 0.1% to about 20%, preferably from about 1% to about 15%, more preferably from about 2% to about 10% by weight.

Optionally, the lipophiilic skin moisturizing agent can be thickened using a thickening agent. Suitable thickening agents for the lipophiilic skin moisturizing agent include polacrylates; fumed silica natural and synthetic waxes, alkyl silicone waxes such as behenyl silicone wax; aluminium silicate; lanolin derivatives such as lanesterol; higher fatty alcohols; polyethylenecopolymers; narogel; polyammonium stearate; sucrose esters; hydrophobic clays; petrolatum; hydrotalcites; and mixtures thereof.

Hydrotalcites are materials of general formula:

where M is a divalent metal ion e.g. $Mg^{2+}$; N is a trivalent metal ion e.g. $Al^{3+}$; X is an exchangeable anion e.g. $CO_3^-$, $NO_3^-$, stearate, cinnimate; m is the number of divalent metal ions; and n is the number of trivalent metal ions.

Particularly preferred thickening agents for the benefit agent include silica, alkyl silicone waxes, paraffin wax higher fatty alcohols, petroleum jelly and polyethylenecopolymers. The thickening agent is preferably from about 4% to about 25% by weight based on the level of the lipophilic skin moisturizing agent.

Whilst some materials can function either as the lipophilic skin moisturizing agent, thickening agent therefor, or detackifying agent, it will be appreciated that the moisturizing, thickening and detackifying function cannot be provided by the same component. However, it will be understood that where the composition comprises three or more lipophilic skin moisturizing agents, two of said lipophilic skin moisturizing agents can also function as a thickening agent or detackifying agent.

Antibacterial Agents

The compositions of the present invention can also, optionally, contain antimicrobial agents. Antimicrobial agents suitable for use in the compositions of the present invention are described in U.S. Pat. Nos. 5,686,089; 5,681, 802, 5,607,980, 4,714,563; 4,163,800; 3,835,057; and 3,152, 181; all of which are herein incorporated by reference in their entirety. When incorporated herein the antimicrobial agent is preferably present at a concentration of from about 0.001% to about 5%, more preferably 0.05% to about 1%, even more preferably from about 0.05% to about 0.5%, and most preferably 0.1% to about 0.5%.

Also useful as antimicrobial agents are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradensis, Berberidaceae daceae, Ratanhiae* and *Curcuma longa*. Also included in this class of natural essential oils are the key chemical components of the plant oils which have been found to provide the antimicrobial benefit. These chemicals include, but are not limited to anethol, catechole, camphene, carvacol, eugenol, eucalyptol, ferulic acid, farnesol, hinokitiol, tropolone, limonene, menthol, methyl salicylate, thymol, terpineol, verbenone, berberine, ratanhiae extract, caryophellene oxide, citronellic acid, curcumin, nerolidol and geraniol.

Additional antimicrobial agents are antibacterial metal salts. This class generally includes salts of metals in groups 3b–7b, 8 and 3a–5a. Specifically are the salts of aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof.

Preferred antimicrobial agents include piroctoneolamine (hereinafter Octopirox®) available from Hoechst AG; 2,4, 4'-trichloro-2'-hydroxy diphenylether (hereinafter "TCS" or Triclosan®") available from Ciba-Geigy Corp.; 3,4,4'-trichlorocarbanilide (hereinafter "TCC" or "Triclocarban®") available from Bayer AG; para-chloro-meta-xylenol (hereinafter PCMX) available from Rhone Poulenc; zinc pyrithione (hereinafter "ZPT") available from the Olin Corp.; 1-phenoxypropan-2-ol available from Nippa Laboratories Ltd.; benzalkonium chlorides and/or substituted benzalkonium chlorides such as those available from Lonza under the tradename Barquat®; benzoyl peroxide, erythromycin, tetracycline, clindamycin, azelaic acid, sulfur compounds such as sulfonamides, resorcinol, essential oils and their key ingredients and mixtures thereof.

Also useful herein is the antimicrobial compositions described in PCT Applications WO98/55080 and WO98/55081, Baier et al., both published Dec. 10, 1998, both of which are herein incorporated by reference in its entirety.

Antifungal Agents

Also useful herein are antifungal agents. Suitable antifungal agents include, in particular compounds belonging to the imidazole class such as clotrimazole, econazole, ketoconazole or miconazole or salts thereof, polyene compounds such as amphotericin B, compounds of the allylamine family such as terbinafine, or octopirox. Also useful herein are naftifine, tolnaftate, amphotericin B, nystatin, 5-fluorocytosine, griseofulvin, and haloprogin. Mixtures of the above antifungals can also be used. A detailed discussion of antifungals as well as additional examples can be found in *Remington's pharmaceutical Sciences*, 17$^{th}$ ed. (Alfonso R. Gennaro ed., 1985) pp. 1225–1231, herein incorporated by reference.

When incorporated herein the antifungal agent is preferably present at a concentration of from about 0.001% to about 5%, more preferably 0.05% to about 1%, even more preferably from about 0.05% to about 0.5%, and most preferably 0.1% to about 0.5%.

Skin Sensates

The skin sanitizing compositions of the present invention may also contain sensates. When used in the present invention, sensates can be present at a level of from about 0.01% to about 10%, typically from about 0.1% to about 5%, and preferably from about 0.2% to about 1%. The level is selected to provide the desired level of consumer perceived sensation and can be modified as desired. Suitable sensate technologies include menthol, eucalyptus, 3-1-menthoxy propane-1,2-diol, N-substituted-p-menthane-3-carboxamides and acyclic carboxamides.

3-1-menthoxy propane 1,2-diol is fully described in detail in U.S. Pat. No. 4,459,425, issued Jul. 10, 1984 to Amano et. al, incorporated herein by reference in its entirety. This volatile aromatic is commercially available, being sold by Takasago Perfumery Co., Ltd., Tokyo, Japan.

The N-substituted-p-menthane-3-carboxamides are fully described in U.S. Pat. No. 4,136,163 to Watson et al., issued Jan. 23, 1979 incorporated herein by reference in its entirety. The most preferred volatile aromatic of this class is N-ethyl-p-menthane-3-carboxamide which is commercially available as WS-3 from Wilkinson Sword Limited.

Useful acyclic carboxamides are fully described in U.S. Pat. No. 4,230,688 to Rowsell et al., issued Oct. 28, 1980 incorporated herein by reference in its entirety. The most preferred volatile aromatic of this class is N,2,3-trimethyl-2-isopropylbutan-amide which is commercially available as WS-23 from Wilkinson Sword Limited.

Perfumes

The compositions of the present invention can also contain perfumes. Suitable perfumes are described in U.S. Pat. No. 5,723,420, herein incorporated by reference in its entirety. Nonlimiting examples of such perfumes include benzaldehyde, benzyl acetate, cis-3-hexenyl acetate, coumarin, dihydromyrcenol, dimethyl benzyl carbinyl acetate, ethyl vanillin, eucalyptol, eugenol, iso eugenol, flor acetate, geraniol, hydroxycitronellal, koavone, linalool, methyl anthranilate, methyl beta naphthyl ketone, methyl dihydro jasmonate, nerol, nonalactone, phenyl ethyl acetate, phenyl ethyl alcohol, alpha terpineol, beta terpineol, vanillin, and mixtures thereof.

When incorporated herein, perfumes are preferably present at concentrations of from about 0.001% to about 1%, more preferably from about 0.01% to about 0.5%, most preferably from about 0.01% to about 0.1%.

Surfactants

Also optional, but preferred, are surfactants or surface active agents. Surfactants can be present in amounts of from about 0.1% to about 5% by weight of the composition. It has been found that any nonionic, anionic, cationic, zwitterionic or amphoteric surfactant, can be used alone, or in combination. Numerous surface active agents or surfactants, suitable for use in the present composition, are described in detail in McCutcheon's "Emulsifiers and Detergents", 1991. Preferably, the surface active agent is present in an amount from about 1.0 to about 30.0% by weight, based on the weight of the composition. Examples of suitable surfactants can be found in U.S. Pat. Nos. 5,624,666 and 5,785,979, both of which are herein incorporated by reference in their entirety.

Particularly preferred for use in the present invention are emulsifying surfactants selected from the group consisting of: emulsifying surfactants having an HLB value below 12 or about 12, preferably, from about 3 to below 12 or about 12, most preferably, from about 3 to about 11 such as steareth-2, PEG- 5 soya sterol oil. PEG 10 soya sterol oil, diethanolamine cetyl phosphate, sorbitan monostearate (Span 60), diethyleneglycol monostearate, glyceryl monostearate, and mixtures thereof; emulsifying surfactants having an HLB value of 12 or above (or about 12 and above) such as Steareth-21, polyoxyethylene sorbitan tristearate (Tween 65), polyethylene glycol 20 sorbitan monostearate, polyethylene glycol 60 sorbitan monostearate, polyethylene glycol 80 sorbitan monostearate. Steareth-20, Ceteth-20, PEG-100 stearate, sodium stearoyl sarcosinate, hydrogenated lecithin, sodium cocoylglyceryl sulfate, sodium stearyl sulfate. sodium stearoyl lactylate, PEG-20 methyl glucoside sesquistearate, PEG-20 glyceryl monostearate, sucrose monostearate, sucrose polystearates (having a high proportion of sucrose monostearate), polyglyceryl 10 stearate, polyglyceryl 10 myristate, steareth 10, DEA oleth 3 phosphate, DEA oleth 10 phosphate, PPG-5 Ceteth 10 phosphate sodium salt. PPG-5 Ceteth 10 phosphate potassium salt, and mixtures thereof; and mixtures thereof. Preferably, the compositions of the present invention comprise at least one emulsifying surfactant having an HLB value below 12 (or below about 12) and at least one emulsifying surfactant having an HLB value of 12 or above (or about 12 or above). "HLB" is well known to one of ordinary skill in the art and means hydrophobic lipophilic balance. See, "The HLB System, A Time-Saving guide to Emulsifier Selection." ICI Americas Inc., August (1984) and McCutcheon's, Detergents and Emulsifiers, North American Edition (1987), published by Mc Publishing Co.; which list various emulifiers useful herein. Both of these references are incorporated herein by reference in their entirety.

The emulifying surfactant comprises from about 0% to about 20%, preferably from about 0.1 to 10%, more preferably, from about 0.25% to about 5%, most preferably, from about 0.25% to about 2.5%.

Skin Care Actives

Skin care actives may also be incorporated into the present invention. Such actives include:

a.) Sunscreen, sunblocks and tanning compositions: Examples of suitable sunscreens, sun blocks and artificial tanning compounds can be found in U.S. Pat. Nos. 5,753,210; 5,603,923 and 5,804,572, all of which are herein incorporated by reference in their entirety;

b.) Irritation reducing agents: Examples of suitable irritation reducing agents include, but are not limited to, corticosteroids such as hydrocortisone, methylprednisolone, dexamethasone, triamcinolone acetconide, and desoxametasone; anesthetics such as benzocaine, dyclonine, lidocaine and tetracaine; antipruitics such as camphor, menthol, oatmeal (colloidal), pramoxine, benzyl alcohol, phenol, panthenol, soluble chitosan and resorcinol. Mixtures of the irritation reducing agents can also be used;

c.) Herbal Ingredients and Plant Extracts: Examples of suitable herbal ingredients and plant extracts can be found in U.S. Pat. Nos. 5,869,540 and 4,767,618, both of which are herein incorporated by reference in their entirety;

d.) Insect Repellants: Suitable insect repellants include, but are not limited to, substituted and unsubstituted hexanediols, substituted toluamides, and synthetic or natural pyretherins. Examples of such insect repellants include, but are not limited to, diethyltoluamide; dimethyl phthalate (DIMP); ethohexadiol (Rutgers 612); dimethyl carbate; indalone; 2,4,4'-trichloro-2'-hydroxydiphenyl ether (Irgasan DP300); salicylic acid; willow extract; N,N'-diethyl-m-toluamide("DEET"); 2-Ethyl-1,3 Hexanediol and mixtures thereof;

e.) Antiinflammatory Agents;

f.) Retinoids;

g.) Antiandrogens;

h.) Anti-oxidants/Radical Scavengers;

i.) Chelators;

j.) Organic hydroxy acids k.) Desquamation agents/exfoliants l.) Depilation agents;

m.) Skin lightening agents; and n.) Zinc salts.

Examples of suitable antiinflammatory agents, retinoids, antiandrogens, anti-oxidants/radical scavengers, chelators, organic hydroxy acids, desquamation agents/exfollients, depilation agents, skin lightening agents, and zinc salts and be found in U.S. Pat. No. 5,833,998 to Biedermann et al., issued Nov. 10, 1998 and PCT Application WO97/39733, Biedermann et al., published Oct. 30, 1997, both of which are herein incorporated by reference in their entirety. Mixtures of the above skin care actives may also be used.

Also useful are antiperspirant actives. Examples of suitable actives can be found in U.S. Pat. No. 5,840,288, Guskey, et al., issued Nov. 24, 1998, herein incorporated by reference in its entirety.

Vitamin

Vitamins may also be incorporated into the compositions of the invention include, but not limited to, vitamin A, pro vitamin A, vitamin B1, vitamin B2, vitamin B3 compounds such as niacinamide and tocopherol nicotinate, vitamin B4, vitamin B5, vitamin B6, vitamin B12, vitamin C, vitamin D, vitamin D2, vitamin D3, vitamin E, vitamin F (cis, cis-linolcic acid), vitamin K1 and combinations and derivatives thereof. Preferred vitamins include vitamins C B and E, as well as derivatives and combinations thereof. In a particularly preferred embodiment, the invention comprises both vitamin C and vitamin E. The vitamins may be present in a concentration from about 0.5–50 percent by weight, preferably 0.5–10 percent by weight, based upon the total weight of the composition.

Film Formers

Also useful herein are film formers. Suitable film formers include, without limitation: acrylamide/sodium acrylate copolymer; ammonium acrylates copolymer; Balsam Peru; cellulose gum; ethylene/maleic anhydride copolymer; hydroxyethylcellulose; hydroxypropylcellulose; polyacrylamide; polyethylene; polyvinyl alcohol; pvm/MA copolymer (polyvinyl methylether/maleic anhydride); PVP (polyvinylpyrrolidone); maleic anhydride copolymer such as PA-18 available from Gulf Science and Technology; PVP/hexadecene copolymer such as Ganex V-216 available from GAF Corporation; acryliclacrylate copolymer; and the like. Examples of other film formers can be found in PCT Applications WO96/33689, Barford et al., published Oct. 31, 1996 and WO98/16196, Dohmae et al., published Apr. 23, 1998, both of which are herein incorporated by reference in their entirety.

Generally, film formers can be present at concentrations of from about 0.1% to about 10% by weight of the composition with from about 1% to about 8% being preferred and from about 0.1% to about 5% being most preferred.

Other Optional Ingredients

The compositions of the present invention can comprise a wide range of optional ingredients. The CTFA International Cosmetic Ingredient Dictionary, Sixth Edition, 1995, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives; colorants such as those described in U.S. Pat. No. 5,843,407 to El-Nokaly, herein incorporated by reference in its entirety; cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

Water-Insoluble Substrates

The compositions of the present invention can also be, optionally, incorporated into a insoluble substrate for application to the skin such as in the form of a treated wipe. Suitable water insoluble substrate materials and methods of manufacture are described in Riedel, "Nonwoven Bonding Methods and Materials," *Nonwoven World* (1987); *The Encyclolpedia Americana*, vol. 11, pp. 147–153, vol. 21, pp. 376–383, and vol. 26, pp. 566–581 (1984); U.S. Pat. No. 4,891,227, to Thaman et al., issued Jan. 2, 1990; U.S. Pat. Nos. 4,891,228 and 5,686,088 to Mitra et al., issued Nov. 11, 1997; U.S. Pat. No. 5,674,591; James et al; issued Oct. 7, 1997, all of which are herein incorporated by reference in their entirety. Preferred substrates are described in PCT Applications WO98/52538, published Nov. 26, 1998; WO98/52537, published Nov. 26, 1998; WO98/18447, published May 7, 1998; WO98/18444, published May 7, 1998; WO98/18442, published May 7, 1998; and WO98/18441, published May 7, 1998, all of which are herein incorporated by reference in their entirety.

Also preferred are hydroentangled web substrates as described in, for example, Evans; U.S. Pat. No. 3,485,786; issued Dec. 23, 1969; Kalwarres; U.S. Pat. No. 2,862,251 and Griswold; U.S. Pat. No. 3,025,585, all of which describe hydroentangling procedures generally and all of which are herein incorporated by reference. See also U.S. Pat. No. 5,674,591; James et al; issued Oct. 7, 1997 which specifically describes a hydroentangling process, including the apparatus used in said process, which can be used to prepare the patterned web. U.S. Pat. No. 5,674,591 is incorporated herein in its entirety.

Methods for Disinfecting and Moisturizing the Skin

The skin sanitizing compositions of the present invention are useful for moisturizing and sanitizing the skin. Generally, the skin disinfection and moisturing process involves topically applying to the skin a safe and effective amount of a composition of the present invention. The present invention can be used when cleansing processes requiring soap and water are unavailable or inconvenient or, alternatively, applied and rinsed off with water. The amount of the composition applied, the frequency of application and the period of use will vary widely depending upon the level of disinfection and moisturization desired, e.g., the degree of microbial contamination and/or degree of skin dryness. Typical amounts of skin sanitizing composition used preferably range from about 0.1 mg/cm$^2$ to about 20 mg/cm$^2$, more preferably from about 0.5 mg/cm$^2$ to about 10 mg/cm$^2$, and most preferably about 1 mg/cm$^2$ to about 5 mg/cm$^2$ of skin area to be cleansed. Preferably, the skin sanitizing compositions of the present invention are used to sanitize and moisturize human and/or animal hands and/or feet.

When additional actives are present, the compositions of the present invention can be applied by use of a patch. Such an approach is particularly useful for problem skin areas needing more intensive treatment or for the transderamal delivery of drugs. The patch can be occlusive, semi-occlusive or non-occlusive. The compositions and actives of the present invention can be contained within the patch or be applied to the skin prior to application of the patch. The patch can also include additional actives such as chemical initiators for exothermic reactions such as those described in PCT application WO 9701313 to Burkett et al. Preferably the patch is applied at night as a form of night therapy. Examples of useful transdermal systems are described in U.S. Pat. Nos. 3,598,122; 3,598,123; 3,731,683; 3,797,494; 4,286,592; 4,314,557; 4,379,454; 4,435,180; 4,559,222; 4,568,343; 4,573,999; 4,588,580; 4,645,502; 4,704,282; 4,816,258; 4,849,226; 4,908,027; 4,943,435; and 5,004,610, all of which are herein incorporated by reference in their entirety. Actives commonly associated with transdermal delivery are disclosed in U.S. Pat. Nos. 5,843,468 and 5,853,751, both of which are herein incorporated by reference in their entirety. It is understood, however, that such actives can be delivered using the present invention even absent a patch.

Article of Manufacture

The present invention also relates to an article of manufacture comprising a dispensing container containing the moisturizing and sanitizing composition. Said dispensing container can be constructed of any of the conventional material employed in fabricating containers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear material, e.g., polyethylene terephthalate.

The dispensing container of the present invention preferably contains instructions for moisturizing and conditioning the skin during the skin sanitation process, wherein the instructions instruct the user to apply the compositions of the present invention to the skin (e.g., the hands) at least 3 times a day, more preferably 5 times a day, most preferably at least 10 times a day.

Also preferred is an article of manufacture wherein the dispensing container is a spray dispenser. Said spray dispenser is any of the manually activated means for producing a spray of liquid droplets as is known in the art. Particularly preferred for use herein are spray dispensers equipped with an electrostatic spray device. Examples of such spray devices are found in U.S. Pat. Nos. 5,494,674; 5,322,684; 5,268,166; 5,490,633; 5,366,553; 5,316,800; 5,292,067; 5,222,663; 5,221,050; 5,184,778; 5,121,884; 4,846,407; 4,663,639; 4,561,037; 4,549,243; 4,356,528; 4,139,155; and 3,873,023, all of which are herein incorporated by reference in their entirety. A preferred spray container is made of clear material, e.g., polyethylene terephthalate.

EXAMPLES

The skin sanitizing compositions illustrated in Examples I-X illustrate specific embodiments of the skin sanitizing compositions of the present invention, but are not intended to be limiting thereof. Other modifications can be undertaken by the skilled artisan without departing from the spirit and scope of this invention.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

Example I

The following is an example of a sanitizing and moisturizing gel of the present invention.

| Ingredient | Amount (weight percent) |
| --- | --- |
| Ethanol[1] | 55 |
| Isopropanol | 3 |
| Biowax 754[2] | 0.4 |
| Carbopol Ultrez 10[3] | 0.3 |
| Carbowax PEG-200[4] | 0.26 |
| Propylene Glycol | 0.02 |
| Aminomethyl Propanol (AMP-95) | 0.15 |
| Perfume | 0.1 |
| Water and minors | q.s. |

[1]200 proof
[2]Dimethicone copolyol, available from Biosil Technologies
[3]Carbomer, available from BF Goodrich
[4]PEG-4, available from Union Carbide In a suitable vessel, the Biowax 754 is dissolved in water and, upon dissolution, Carbopol Ultrez 10 is added with stirring. Next, the ethanol, isopropanol, Carbowax PEG-200, propylene glycol and perfume are added. Finally, aminomethyl propanol is added to form a thickened clear gel with low tackiness.

Example II

The following is an example of an odor controlling, sanitizing and moisturizing gel of the present invention.

| Ingredient | Amount (weight percent) |
| --- | --- |
| Ethanol | 55 |
| Isopropanol | 3 |
| Alpha-cyclodextrin | 0.6 |
| Biowax 754 | 0.4 |
| Carbopol Ultrez 10 | 0.3 |
| Carbowax PEG-200 | 0.26 |
| Propylene Glycol | 0.02 |
| Aminomethyl Propanol (AMP-95) | 0.15 |
| Perfume | 0.1 |
| Water and minors | q.s. |

In a suitable vessel, the alpha-cyclodextrin and Carbowax PEG-4 are dissolved in water and, upon dissolution, Carbopol Ultrez 10 is added with stirring. Next, the ethanol, isopropanol, Carbowax PEG-200, propylene glycol and perfume are added. Finally, aminomethyl propanol is added to form a thickened clear gel with low tackiness and improved odor control.

Example III

The following is an example of a sanitizing and moisturizing solution of the present invention.

| Ingredient | Amount (weight percent) |
| --- | --- |
| Ethanol | 55 |
| Isopropanol | 3 |
| Biowax 754 | 1 |
| Glycerin | 5 |
| Propylene Glycol | 0.02 |
| Perfume | 0.1 |
| Water and minors | q.s. |

In a suitable vessel, the Biowax 754 is dissolved in water. Next, the ethanol, isopropanol, propylene glycol and perfume are added to form a clear solution having reduced tackiness.

Example IV

The following is an example of an odor controlling, sanitizing and moisturizing gel of the present invention.

| Ingredient | Amount (weight percent) |
| --- | --- |
| Ethanol | 55 |
| Isopropanol | 3 |
| Alpha-Cyclodextrin | 0.6 |
| Carbowax 1450[1] | 1 |
| Carbopol Ultreaz 10 | 0.3 |
| Glycerin | 5 |
| Propylene Glycol | 0.02 |
| Perfume | 0.1 |
| Aminomethyl Propanol | 0.15 |

-continued

| Ingredient | Amount (weight percent) |
| --- | --- |
| (AMP-95) | |
| Water and minors | q.s. |

[1]PEG-32, available from Union Carbide

In a suitable vessel, the alpha-cyclodextrin and Biowax 754 are dissolved in water and, upon dissolution, Carbopol Ultrez 10 is added with stirring. Next, the ethanol, isopropanol, glycerin, propylene glycol and perfume are added. Finally, aminomethyl propanol is added to form a thickened gel with low tackiness and improved odor control.

Example V

The following is an example of an odor controlling, sanitizing and moisturizing gel of the present invention.

| Ingredient | Amount (weight percent) |
| --- | --- |
| Ethanol | 55 |
| Isopropanol | 3 |
| SFE839[1] | 8 |
| Alpha-Cyclodextrin | 0.6 |
| Carbopol Ultreaz 10 | 0.3 |
| Glycerin | 5 |
| Propylene Glycol | 0.02 |
| Perfume | 0.1 |
| Aminomethyl Propanol (AMP-95) | 0.15 |
| Water and minors | q.s. |

[1]Silicone elastomer dispersion (cyclomethicone [and] dimethicone/vinyldimethicone crosspolymer), available from GE In a suitable vessel, the alpha-cyclodextrin is dissolved in water and, upon dissolution, Carbopol Ultrez 10 is added with stirring. Next, the ethanol, isopropanol, glycerin, propylene glycol, SFE839 and perfume are added. Finally, aminomethyl propanol is added to form a thickened gel with low tackiness and improved odor control.

Example VI

The following is an example of an odor controlling, sanitizing and moisturizing gel of the present invention.

| Ingredient | Amount (weight percent) |
| --- | --- |
| Ethanol | 55 |
| Isopropanol | 3 |
| Tospearl 145A[1] | 1 |
| Alpha cyclodextrin | 0.6 |
| Carbopol Ultreaz 10 | 0.3 |
| Glycerin | 5 |
| Propylene Glycol | 0.02 |
| Perfume | 0.1 |
| Aminomethyl Propanol (AMP-95) | 0.15 |
| Water and minors | q.s. |

[1]Particulate crosslinked hydrocarbyl-substituted polysiloxane, available from Toshiba Silicone In a suitable vessel, the alpha-cyclodextrin is dissolved in water and, upon dissolution, Carbopol Ultrez 10 is added with stirring. Next, the ethanol, isopropanol, glycerin, propylene glycol, Tospearl 145A and perfume are added. Finally, aminomethyl propanol is added to form a thickened gel with low tackiness and improved odor control.

Example VII

The following is an example of an odor controlling, sanitizing and moisturizing gel of the present invention.

| Ingredient | Amount (weight percent) |
| --- | --- |
| Ethanol | 55 |
| Isopropanol | 3 |
| Cyclomethicone (D-5)[1] | 8 |
| Alpha cyclodextrin | 0.6 |
| Carbopol Ultreaz 10 | 0.3 |
| Glycerin | 5 |
| Propylene Glycol | 0.02 |
| Perfume | 0.1 |
| Aminomethyl Propanol (AMP-95) | 0.15 |
| Water and minors | q.s. |

[1]SF1202 (D5) fluid, available from GE

In a suitable vessel, the alpha-cyclodextrin is dissolved in water and, upon dissolution, Carbopol Ultrez 10 is added with stirring. Next, the ethanol, isopropanol, glycerin, propylene glycol, cyclomethicone (D-5) and perfume are added. Finally, aminomethyl propanol is added to form a thickened gel with low tackiness and improved odor control.

Example VIII

The following is an example of a sanitizing and moisturizing gel of the present invention.

| Ingredient | Amount (weight percent) |
| --- | --- |
| Ethanol | 55 |
| Isopropanol | 3 |
| SFE839 | 8 |
| Biowax 754 | 0.4 |
| Carbopol Ultreaz 10 | 0.3 |
| Glycerin | 5 |
| Propylene Glycol | 0.02 |
| Perfume | 0.1 |
| Aminomethyl Propanol (AMP-95) | 0.15 |
| Water and minors | q.s. |

In a suitable vessel, the Biowax 754 is dissolved in water and, upon dissolution, Carbopol Ultrez 10 is added with stirring. Next, the ethanol, isopropanol, glycerin, propylene glycol, SFE839 and perfume are added. Finally, aminomethyl propanol is added to form a thickened gel with reduced tackiness.

Example IX

The following is an example of a sanitizing and moisturizing gel of the present invention.

| Ingredient | Amount (weight percent) |
| --- | --- |
| Ethanol | 55 |
| Isopropanol | 3 |
| Tospearl 145A | 1 |
| Biowax 754 | 0.4 |
| Carbopol Ultreaz 10 | 0.3 |
| Glycerin | 5 |
| Propylene Glycol | 0.02 |
| Perfume | 0.1 |

| Ingredient | Amount (weight percent) |
| --- | --- |
| Aminomethyl Propanol (AMP-95) | 0.15 |
| Water and minors | q.s. |

In a suitable vessel, the Biowax 754 is dissolved in water and, upon dissolution, Carbopol Ultrez 10 is added with stirring. Next, the ethanol, isopropanol, glycerin, propylene glycol, Tospearl 145A and perfume are added. Finally, aminomethyl propanol is added to form a thickened gel with reduced tackiness.

Example X

The following is an example of a sanitizing and moisturizing gel of the present invention.

| Ingredient | Amount (weight percent) |
| --- | --- |
| Ethanol | 55 |
| Isopropanol | 3 |
| Cyclomethicone (D-5) | 8 |
| Biowax 754 | 0.4 |
| Carbopol Ultreaz 10 | 0.3 |
| Glycerin | 5 |
| Propylene Glycol | 0.02 |
| Perfume | 0.1 |
| Aminomethyl Propanol (AMP-95) | 0.15 |
| Water and minors | q.s. |

In a suitable vessel, the Biowax 754 is dissolved in water and, upon dissolution, Carbopol Ultrez 10 is added with stirring. Next, the ethanol, isopropanol, glycerin, propylene glycol, cyclomethicone (D-5) and perfume are added. Finally, aminomethyl propanol is added to form a thickened gel with reduced tackiness.

What is claimed is:

1. A skin sanitizing composition, comprising a continuous phase comprising:
    a.) an effective amount of sanitizing agent to kill or reduce the growth of microorganisms, the sanitizing agent comprising from about 40% to about 99% by weight of the composition of alcohol antiseptic;
    b.) from about 0.1% to about 15% of a humectant;
    c.) an effective amount of a detackifying agent selected from the group consisting of:
        i.) wax material soluble in the alcohol antiseptic and having a melting point greater than about 20° C.;
        ii.) silicones selected from the group consisting of nonvolatile silicones having a viscosity of at least about 15,000 centipoise, silicone elastomer, silicone elastomer/volatile silicone blends, silicone elastomer/nonvolatile silicone blends, nonvolatile/volatile silicone blends and mixtures thereof;
        iii.) powder;
        iv.) fluorochemicals; and
        v.) mixtures thereof;
    d.) optionally, from 0 to about 10% of thickener;
    e.) optionally, from 0 to about 20% of a lipophilic skin moisturizing agent;
    f.) optionally, from 0 to about 1% of perfume; and
    g.) from about 0 to about 60% water.

2. A skin sanitizing composition according to claim 1, wherein said humectant is selected from the group consisting of ethylene glycol, propylene glycol, dipropylene glycol, butylene glycol, hexylene glycol, polyethylene glycols, glycerin sorbitol, panthenols, urea, alkoxylated glucose derivatives, hexanetriol, glucose ethers, sodium hyaluronate, polyethylene.

3. A skin sanitizing composition according to claim 1, wherein said detackifying agent is a wax material soluble in the continuous phase and having a melting point greater than about 20° C.

4. A skin sanitizing composition according to claim 3, wherein said wax material selected from the group consisting of dimethicone copolyols, polyethylene glycols and mixtures thereof.

5. A skin sanitizing composition according to claim 1, wherein the alcohol antiseptic is selected from the group consisting of ethanol, n-propanol and isopropanol and mixtures thereof.

6. A skin sanitizing composition according to claim 5, wherein the alcohol antiseptic is ethanol.

7. A skin sanitizing composition according to claim 1, further comprising a cyclodextrin selected from the group consisting of alpha-cyclodextrin, methylated alpha-cyclodextrin, methylated beta-cyclodextrin, hydroxyethyl alpha-cyclodextrin, hydroxyethyl beta-cyclodextrin, hydroxypropyl alpha-cyclodextrin, hydroxypropyl beta-cyclodextrin, and mixtures thereof.

8. A skin sanitizing composition according to claim 1, further comprising an odor control agent selected from the group consisting of zeolites, soluble carbonate and/or bicarbonate salts, water soluble ionic polymers, silica gel, silica molecular sieves, activated alumina, kieselguhr, fullers earth, montmorillonite, smectite, attapulgite, bentonite, palygorskite, kaolinite, illite, halloysite, hectorite, beidellite, nontronite, saponite, hormite, vermiculite, sepiolite, chlorophyll, soda lime, calcium oxide, chitin, potassium permanganate, and activated charcoal or activated carbon and mixtures thereof.

9. A skin sanitizing composition according to claim 1, wherein the lipophilic skin moisturizing agent is present at a concentration of from about 0.1% to about 20%.

10. A skin sanitizing composition according to claim 9, wherein the lipophilic skin moisturizing agent is selected from the group consisting of petrolatum, mineral oil, microcrystalline waxes, polyalkenes, paraffin, cerasin, ozokerite, polyethylene, perhydrosqualene, dimethicones, cyclomethicones, alkyl siloxanes, polymethylsiloxanes, methylphenylpolysiloxanes, hydroxylated milk glyceride, castor oil, soy bean oil, maleated soy bean oil, safflower oil, cotton seed oil, corn oil, walnut oil, peanut oil, olive oil, cod liver oil, almond oil, avocado oil, palm oil, sesame oil, liquid sucrose octaesters, blends of liquid sucrose octaesters and solid polyol polyesters, lanolin oil, lanolin wax, lanolin alcohol, lanolin fatty acid, isopropyl lanolate, acetylated lanolin, acetylated lanolin alcohols, lanolin alcohol linoleate, lanolin alcohol riconoleate, beeswax, beeswax derivatives, spermaceti, myristyl myristate, stearyl stearate, carnauba and candelilla waxes, cholesterol, cholesterol fatty acid esters and homologs thereof, lecithin and derivatives, Sphingo lipids, ceramides, glycosphingo lipids and homologs thereof, and mixtures thereof.

11. A skin sanitizing composition according to claim 1, wherein the thickener is present at a concentration of from about 0.1% to about 5%.

12. A skin sanitizing composition according to claim 11, wherein the thickener is selected from the group consisting of carbomers, sodium alginate, xanthan gum, quince seed extract, tragacanth gum, starch, hydroxyethyl cellulose, methyl cellulose, carboxymethyl cellulose, hydroxy propylmethyl cellulose, polyvinylpyrrolidone, polyvinylalcohol, guar gum, hydroxypropyl guar gum, soluble starch, cationic celluloses, cationic guars, carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers, aluminium silicates, bentonites, mixtures of polyethylene glycol and polyethylene glycol stearate or distearate, hydrophobically modified celluloses and mixtures thereof.

13. A skin sanitizing composition according to claim 1, further comprising a perfume.

14. A skin sanitizing composition according to claim 13, wherein the perfume is selected from the group consisting of benzaldehyde, benzyl acetate, cis-3-hexenyl acetate, coumarin, dihydromyrcenol, dimethyl benzyl carbinyl acetate, ethyl vanillin, eucalyptol, eugenol, iso eugenol, flor acetate, geraniol, hydroxycitronellal, koavone, linalool, methyl anthranilate, methyl beta naphthyl ketone, methyl dihydro jasmonate, nerol, nonalactone, phenyl ethyl acetate, phenyl ethyl alcohol, alpha terpineol, beta terpineol, vanillin, and mixtures thereof.

15. A skin sanitizing composition according to claim 1 further comprising a skin sensate.

16. A skin sanitizing composition according to claim 15, wherein the skin sensate is selected from the group consisting of menthol, eucalyptus, 3-1-menthoxy propane-1,2-diol, N-substituted-p-menthane-3-carboxamides and acyclic carboxamides.

17. A skin sanitizing composition according to claim 1, further comprising an emulsifying surfactant.

18. A skin sanitizing composition according to claim 17, wherein the emulsifying surfactant comprises at least one emulsifying surfactant having an HLB value below 12 and at least one emulsifying surfactant having an HLB value of 12 or above.

19. A skin sanitizing composition, comprising:
   a.) an effective amount of sanitizing agent to kill or reduce the growth of microorganisms, the sanitizing agent comprising from about 40% to about 99% by weight of the composition of alcohol antiseptic;
   b.) from about 0.1 to about 10% of a thickening agent;
   c.) an effective amount of a detackifying agent selected from the group consisting of:
      i.) wax material soluble in the alcohol antiseptic and having a melting point greater than about 20° C.;
      ii.) silicones selected from the group consisting of nonvolatile silicones having a viscosity of at least about 15,000 centipoise, silicone elastomer, silicone elastomer/volatile silicone blends, silicone elastomer/nonvolatile silicone blends, nonvolatile/volatile silicone blends and mixtures thereof;
      iii.) powder;
      iv.) fluorochemicals; and
      v.) mixtures thereof;
   d.) optionally, from 0 to about 20% of a lipophilic skin moisturizing agent;
   e.) optionally, from 0 to about 1% of perfume; and
   f.) from about 0 to about 60% water.

20. A skin sanitizing composition, comprising:
   a.) an effective amount of sanitizing agent to kill or reduce the growth of microorganisms, the sanitizing agent comprising from about 40% to about 99% by weight of the composition of alcohol antiseptic;
   b.) from about 0.1% to about 15% of a humectant;
   c.) at least about 3% of a volatile silicone detackifying agent, wherein said silicone detackifying agent has a surface tension of less than about 35 dynes;
   d.) optionally, from 0 to about 10% of thickener;
   e.) optionally, from 0 to about 20% of a lipophilic skin moisturizing agent;
   f.) optionally, from 0 to about 1% of perfume; and
   g.) from about 0 to about 60% water.

21. A skin sanitizing and moisturizing wipe, comprising:
A.) one or more layers of water-insoluble substrate; and
B.) a safe and effective amount of skin sanitizing composition, comprising
   a.) an effective amount of sanitizing agent to kill or reduce the growth of microorganisms, the sanitizing agent comprising from about 40% to about 99% by weight of the composition of alcohol antiseptic;
   b.) from about 0.1% to about 15% of a humectant;
   c.) an effective amount of a detackifying agent selected from the group consisting of:
      i.) wax material soluble in the alcohol antiseptic and having a melting point greater than about 20° C.;
      ii.) silicones selected from the group consisting of nonvolatile silicones having a viscosity of at least about 15,000 centipoise, silicone elastomer, silicone elastomer/volatile silicone blends, silicone elastomer/nonvolatile silicone blends, nonvolatile/volatile silicone blends and mixtures thereof;
      iii.) powder;
      iv.) fluorochemicals; and
      v.) mixtures thereof;
   d.) optionally, from 0 to about 10% of thickener;
   e.) optionally, from 0 to about 20% of a lipophilic skin moisturizing agent;
   f.) optionally, from 0 to about 1% of perfume; and
   g.) from about 0 to about 60% water.

22. A method of sanitizing and moisturizing skin, by applying to skin a safe and effective amount of the composition of claim 1.

23. A method of sanitizing and moisturizing skin by applying to skin the sanitizing and moisturizing wipe of claim 21.

24. An article of manufacture, comprising a container containing a skin sanitizing composition, comprising
   a.) an effective amount of sanitizing agent to kill or reduce the growth of microorganisms, the sanitizing agent comprising from about 40% to about 99% by weight of the composition of alcohol antiseptic;
   b.) from about 0.1% to about 15% of a humectant;
   c.) an effective amount of a detackifying agent selected from the group consisting of:
      i.) wax material soluble in the alcohol antiseptic and having a melting point greater than about 20° C.;
      ii.) silicones selected from the group consisting of nonvolatile silicones having a viscosity of at least about 15,000 centipoise, silicone elastomer, silicone elastomer/volatile silicone blends, silicone elastomer/nonvolatile silicone blends, nonvolatile/volatile silicone blends and mixtures thereof;
      iii.) powder;
      iv.) fluorochemicals; and
      v.) mixtures thereof;
   d.) optionally, from 0 to about 10% of thickener;
   e.) optionally, from 0 to about 20% of lipophilic skin moisturizing agent;

f.) optionally, from 0 to about 1% of perfume; and g.) from about 0 to about 60% water;

wherein said container has instructions for moisturizing and conditioning the skin during the skin sanitizing process, said instructions comprising instruction to apply the skin sanitizing composition to skin and then rub or massager the composition onto the skin at least 3 times a day.

25. An article of manufacture, comprising a container containing a skin sanitizing composition, comprising:

a.) an effective amount of sanitizing agent to kill or reduce the growth of microorganisms, the sanitizing agent comprising from about 40% to about 99% by weight of the composition of alcohol antiseptic;

b.) from about 0.1% to about 15% of a humectant;

c.) optionally, from 0 to about 10% of thickener;

d.) optionally, from 0 to about 20% of lipophilic skin moisturizing agent;

e.) optionally, from 0 to about 1% of perfume; and f.) from about 0 to about 60% water wherein said container has instructions for moisturizing and conditioning the skin during the skin sanitizing process, said instructions comprising instruction to apply the skin sanitizing composition to skin and then rub or massage the composition onto the skin at least 3 times a day.

* * * * *

UNITED STATES PATENT AND TRADEMARK OFFICE
CERTIFICATE OF CORRECTION

PATENT NO. : 6,423,329 B1
DATED : July 23, 2002
INVENTOR(S) : Mark Richard Sine et al.

It is certified that error appears in the above-identified patent and that said Letters Patent is hereby corrected as shown below:

Column 2,
Line 50, after "Preferably" insert -- , --.

Column 3,
Line 29, "identical" should read -- identified --.

Column 4,
Line 52, first occurrence "Coming" should read -- Corning --.
Line 52, second occurrence "Coming" should read -- Corning --.
Line 53, "Coming" should read -- Corning --.
Line 54, "Coming" should read -- Corning --.

Column 8,
Line 47, "vermniculite" should read -- vermiculite --.

Column 10,
Line 25, "satffower" should read -- safflower --.

Column 13,
Line 32, "." should read -- , --.
Line 32, "PEG 10" should read -- PEG-10 --.
Lines 40, 43, 49 and 58, "." should read -- , --.
Line 61, "emulifiers" should read -- emulsifiers --.
Line 64, "emulifying" should read -- emulsifying --.
Line 65, after "0.1" insert -- % --.

Column 14,
Line 65, "linolcic" should read -- linoleic --.

Column 15,
Line 64, "Encyclolpedia" should read -- Encyclopedia --.

UNITED STATES PATENT AND TRADEMARK OFFICE
CERTIFICATE OF CORRECTION

PATENT NO. : 6,423,329 B1
DATED : July 23, 2002
INVENTOR(S) : Mark Richard Sine et al.

It is certified that error appears in the above-identified patent and that said Letters Patent is hereby corrected as shown below:

<u>Column 24,</u>
Line 38, delete ",".

<u>Column 25,</u>
Line 6, "massager" should read -- massage --.

Signed and Sealed this

Twelfth Day of November, 2002

Attest:

JAMES E. ROGAN
*Attesting Officer*     *Director of the United States Patent and Trademark Office*